United States Patent
Mazereeuw et al.

(10) Patent No.: US 8,779,241 B2
(45) Date of Patent: Jul. 15, 2014

(54) **CUCUMBER VEIN YELLOWING VIRUS (CVYV) RESISTANT CUCUMBER PLANTS (*CUCUMIS SATIVUS* L.)**

(75) Inventors: Jaap Mazereeuw, Enkhuizen (NL); Brigit Van Kampen, Horst (NL); Ronald Wilterdink, Enkhuizen (NL); Nanne Faber, Hoorn (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 124 days.

(21) Appl. No.: 13/382,770

(22) PCT Filed: Jul. 7, 2009

(86) PCT No.: PCT/EP2009/058570
§ 371 (c)(1),
(2), (4) Date: Feb. 15, 2012

(87) PCT Pub. No.: WO2011/003440
PCT Pub. Date: Jan. 13, 2011

(65) Prior Publication Data
US 2012/0137388 A1    May 31, 2012

(51) Int. Cl.
*A01H 1/02* (2006.01)
*A01H 1/04* (2006.01)
*A01H 5/08* (2006.01)

(52) U.S. Cl.
USPC .......... 800/307; 800/266; 800/265; 800/267; 435/6.11

(58) Field of Classification Search
None
See application file for complete search history.

(56) References Cited

U.S. PATENT DOCUMENTS

2008/0244785 A1   10/2008   Mazereeuw et al.

FOREIGN PATENT DOCUMENTS

| EP | 0534858 A1 | 3/1993 |
|---|---|---|
| WO | 2009059777 A1 | 5/2009 |
| WO | 2009086850 A1 | 7/2009 |

OTHER PUBLICATIONS

Slate (Molecular Ecology (2005) 14, pp. 363-379).*
Pico et al. (Journal of Virological Methods, 128, (2005) 14-20).*
Pico et al. (2) (Modern Variety Breeding for Present and Future Needs (2008)).*
Michelmore et al. (Proc. Natl. Acad. Sci. USA. vol. 88, pp. 9828-9832. (1991)).*
Martin et al. (Virology, vol. 94, No. 1, 2004, pp. 111-119).*
Vos et al., "AFLP: a new technique for DNA fingerprinting", Nucleic Acids Research, 1995, pp. 4407-4414, vol. 23, No. 21.
Pico et al., "Screening *Cucumis sativus* landraces for resistance to cucumber vein yellowing virus", Plant Breeding, 2003, pp. 426-430, vol. 122.
Pico et al., "Genetics of the resistance to CVYV in cucumber", Proceedings of the 18th EUCARPIA general congress, Sep. 9, 2008, one page, (Abstract Only).

* cited by examiner

*Primary Examiner* — Brent T Page
*Assistant Examiner* — Jared Shapiro
(74) *Attorney, Agent, or Firm* — The Webb Law Firm

(57) ABSTRACT

Molecular markers genetically linked to, and capable of identifying, a genetic locus in the cucumber plant (*Cucumis sativus* L.) genome conferring a general resistance against tobamoviruses, and especially against two commercially important pathogenic tobamoviruses, i.e., cucumber green mottle mosaic virus (CGMMV) and cucumber fruit mottle mosaic virus (CFMMV) are provided. Methods for providing a cucumber plant (*Cucumis sativus* L.,) plants, plant parts and fruits with resistance against tobamoviruses and especially against two commercially important pathogenic tobamoviruses, i.e., cucumber green mottle mosaic virus (CGMMV) and cucumber fruit mottle mosaic virus (CFMMV) are also provided.

3 Claims, No Drawings

CUCUMBER VEIN YELLOWING VIRUS (CVYV) RESISTANT CUCUMBER PLANTS (*CUCUMIS SATIVUS* L.)

REFERENCE TO A "SEQUENCE LISTING," A TABLE, OR A COMPUTER PROGRAM LISTING APPENDIX

The Sequence Listing associated with this application is filed in electronic format via EFS-Web and is hereby incorporated by reference into the specification in its entirety. The name of the text file containing the Sequence Listing is 2HQ92_ST25.txt. The size of the text file is 4,096 bytes, and the text file was created Dec. 14, 2011.

BACKGROUND OF THE INVENTION

The present invention relates to Cucumber Vein Yellowing Virus (CVYV) resistant cucumber plants (*Cucumis sativus* L.), methods for providing Cucumber Vein Yellowing Virus (CVYV) resistant cucumber plants (*Cucumis sativus* L.), molecular markers for use in the method, and plants, plant parts, tissues, cells and/or seeds derived from, or originating from, the present Cucumber Vein Yellowing Virus (CVYV) resistant cucumber plants (*Cucumis sativus* L.).

Cucumber plants, i.e., plants of the botanical species *Cucumis sativus*, belong to the gourd family of Cucurbitaceae, also comprising family members like melons and squash. The edible fruits of the plant are generally designated as cucumbers.

Cucumbers usually are cylindrical, green skinned fruits, comprising approximately 96% water. The cucumber plant, also designated as *Cucumis sativus* L., which has been cultivated since long, is an important horticultural crop worldwide. Cucumbers are commonly harvested in an unripe stadium and may be used for the pickle industry or the fresh market.

Cucumber Vein Yellowing Virus, also abbreviated as CVYV, belongs to the *Ipomovirus* genus of the family of the Potyviridae. It is a rather unstable virus with rod-shaped particles, generally being 740-800 nm long and 15-18 nm wide. The viral nucleic acid of CVYV has been reported to consist of double stranded RNA.

The virus has a narrow host range that is mainly restricted to plants of the family of Cucurbitaceae. This family includes economic important crops like cucumbers, squashes (including pumpkins), melons and watermelons. Although CVYV infections generally are a major problem in cucumber production, also squash, zucchini, watermelon and melon productions are affected.

CVYV is generally transmitted by the whitefly *Bremisia tabaci*. CVYV infected plants generally show vein yellowing or vein clearing and stunting with corresponding yield reduction. CVYV infection may also cause death of the plants.

Thus, CVYV can have disastrous effects in crops when they become contaminated. Prevention of infection, by, for example, raising seedlings in a whitefly free environment, or treatment using, for example, pesticides, generally is costly and/or unfriendly to the environment. In addition, these methods do not always provide satisfactory results.

Cucumber Green Mottle Mosaic Virus, also abbreviated as CGMMV, is a RNA virus of the tobamovirus genus causing a severe disease of Cucurbits. Strains of CGMMV were first reported from the United Kingdom and Europe. The virus is present in all tissues and the virus is rapidly transmitted by workers hands, clothing, knives and other equipment and is additionally seed-borne. Heat treatment of seeds is commonly used to control viral contamination. CGMMV is also capable of spreading via surface water. Symptoms of yellowing, mottling and down-curling of the leaves have been reported though perhaps most significant are reports of moderate to severe fruit mottling and distortion. Such mottling and distortion of the fruits could quickly render infected crops unmarketable.

Cucumber Green Mottle Mosaic Virus is perhaps the most widespread and renowned of the tobamoviruses infecting cucumber crops. CGMMV is a worldwide problem in cucumber production areas like The Netherlands, Spain, Greece and India. Yield losses may be a much as 15%.

Cucumber Fruit Mottle Mosaic Virus, also abbreviated as CFMMV, is another family member of the tobamoviruses causing significant economic damage to cucumber plants (*Cucumis sativus* L). Symptoms of Cucumber Fruit Mottle Mosaic virus (CFMMV) infections are generally first recognized on fruits and apical leaves at a relatively advanced growth stage. Leaf symptoms include severe mosaic, vein banding and yellow mottling. In some cases, fully developed plants show severe wilting symptoms that lead to plant collapse. Rapid viral spread within greenhouses may lead to significant crop losses.

Considering the economic damages caused by Cucumber Vein Yellowing Virus(CVYV) in cucumber plants (*Cucumis sativus* L.), it is an object, amongst other objects, of the present invention to provide Cucumber Vein Yellowing Virus (CVYV) resistant cucumber plants (*Cucumis sativus* L.).

Further, it is an object, amongst other objects, of the present invention to provide methods and means for providing Cucumber Vein Yellowing Virus (CVYV) resistant cucumber plants (*Cucumis sativus* L.).

SUMMARY OF THE INVENTION

The above objects, amongst other objects, are met by the present invention by a method as described in the appended claim 1.

Specifically, the above objects, amongst other objects, are met by the present invention by a method for providing a Cucumber Vein Yellowing Virus, or CVYV, resistant cucumber plant, or Cucumis sativus L., comprising:
  a) selecting a first cucumber plant (*Cucumis sativus* L.), wherein said selection comprises establishing the presence of a Cucumber Vein Yellowing Virus (CVYV) resistance conferring genetic element by detecting a nucleic acid amplification fragment of 245 to 247 base pairs, preferably 246 base pairs, using molecular amplified fragment length polymorphism (AFLP) primers SEQ ID No: 1 and SEQ ID No: 2 in a molecular amplified fragment length polymorphism (AFLP) assay using the genome of said first cucumber plant (*Cucumis sativus* L.) as a template;
  b) transferring the identified Cucumber Vein Yellowing Virus (CVYV) resistance conferring genetic element into a second cucumber plant (*Cucumis sativus* L.) thereby conferring Cucumber Vein Yellowing Virus (CVYV) resistance to said second cucumber plant (*Cucumis sativus* L.), wherein said transferring comprises detecting a nucleic acid amplification fragment of 245 to 247 base pairs. Preferably 246 base pairs, using molecular amplified fragment length polymorphism (AFLP) primers SEQ ID No: 1 and SEQ ID No: 2 in a molecular amplified fragment length polymorphism (AFLP) assay using the genome of said second cucumber plant (*Cucumis sativus* L.) as a template.

According to the present invention, primer SEQ ID No: 1 comprises the nucleic acid sequence:

```
5'-GAC TGC GTA CCA ATT CGT-3'
``` and primer SEQ ID No: 2 comprises the nucleic acid sequence:

```
5'-GAT GAG TCC TGA GTA ACA C-3'
```

DESCRIPTION OF THE PREFERRED EMBODIMENTS

The present nucleic acid amplification fragment indicating the presence of a Cucumber Vein Yellowing Virus (CVYV) resistance conferring genetic element is generally designated in the art as an Amplified Fragment Length Polymorphism (ALFP) marker genetically linked to the present Cucumber Vein Yellowing Virus (CVYV) resistance conferring genetic element and is interchangeably designated herein as Marker E22/M48-F-246 with a nucleic acid size of 245 to 247 base pairs, preferably 246 base pairs.

The present nucleic acid amplification fragment of 245 to 247 base pairs, preferably 246 base pairs, and thereby the present Cucumber Vein Yellowing Virus (CVYV) resistance conferring genetic element, can be identified, or detected, using any suitable amplification technique for plant genomic material such as PCR.

In a particularly preferred embodiment, present nucleic acid amplification fragment of 245 to 247 base pairs, preferably 246 base pairs, and thereby the present Cucumber Vein Yellowing Virus (CVYV) resistance conferring genetic element, is identified, or detected, using a nucleic acid amplification technique designated in the art as Molecular Amplified Fragment Length Polymorphism (ALFP, Vos, P., Hogers, R, Bleeker, M., et al. 1995. AFLP: a new technique for DNA fingerprinting. Nucleic Acids Research 23(21): 4407-4414; Zabeau, M and P. Vos. 1993. Selective restriction fragment amplification: a general method for DNA fingerprinting. European Patent Office, publication EP 0 534 858 A1)

Amplified fragment length polymorphism (AFLP) is a polymerase chain reaction (PCR) based genetic fingerprinting technique that was developed in the early 1990's by Keygene, the Netherlands. Briefly, AFLP uses restriction enzymes to digest genomic DNA, followed by ligation of complementary double stranded adaptors to the ends of the restriction fragments. A subset of the restriction fragments are then amplified using 2 primers complementary to the adaptor and restriction site fragments. The fragments are visualized on denaturing polyacrylamide gels either through autoradiographic or fluorescence methodologies.

This generally results in the visualization of a multitude of nucleic acid amplification fragments of different sizes. By comparing the nucleic acid amplification fragments obtained from, for example, susceptible and resistant plants, discriminating nucleic acid amplification fragments can be identified, also designated as markers, between both +phenotypes.

In the present case, a specific AFLP marker, designated as AFLP Marker E22/M48-F-246, genetically linked to, and capable of identifying, the present resistance locus was identified by the presence of a nucleic acid amplification fragment of 245-247 bp, preferably 246 bp. This marker was only present, amongst a number of non-discriminative other AFLP amplification fragments, in the resistant individuals and absent in the susceptible individuals.

It should be noted that AFLP analysis of cucumber plants (*Cucumis sativus* L.) using AFLP primers SEQ ID Nos: 1 and 2, in order to identify the present Cucumber Vein Yellowing Virus (CVYV) resistance conferring genetic element in a first cucumber plant (*Cucumis sativus* L.), can yield a second nucleic acid amplification fragment having a small size difference with the present AFLP Marker E22/M48-F-246. According to the present invention, this larger nucleic acid amplification fragment is not genetically linked to, and capable of identifying, the present Cucumber Vein Yellowing Virus (CVYV) resistance conferring genetic element.

In other words, the present first cucumber plant (*Cucumis sativus* L.), when analyzed using AFLP and AFLP primers SEQ ID Nos: 1 and 2, must yield the present AFLP E22/M48-F-246 marker of the indicated size, but can, additionally, also yield a second nucleic acid amplification fragment of larger size, i.e., 248 to 250 by such as 248 base pairs.

The first cucumber plant (*Cucumis sativus* L.) according to the present invention can be any cucumber plant (*Cucumis sativus* L.) plant having a resistant phenotype for Cucumber Vein Yellowing Virus (CVYV), conferred by the present Cucumber Vein Yellowing Virus (CVYV) resistance conferring genetic element and identifiable by the nucleic acid amplification fragment as described above.

The present selection of a first cucumber plant (*Cucumis sativus* L.) inherently comprises the detection of the present Cucumber Vein Yellowing Virus (CVYV) resistance conferring genetic element in this plant using molecular biology techniques.

After identifying, establishing, or detecting the present Cucumber Vein Yellowing Virus (CVYV) resistance conferring genetic element in a first cucumber plant (*Cucumis sativus* L.), the genetic element is transferred into a second cucumber plant (*Cucumis sativus* L.) thereby conferring Cucumber Vein Yellowing Virus (CVYV) resistance to said second cucumber plant (*Cucumis sativus* L.).

Preferably, transferring the Cucumber Vein Yellowing Virus (CVYV) resistance conferring genetic element comprises conventional breeding methods such as conventional crossing the first cucumber plant (*Cucumis sativus* L.) with the second cucumber plant (*Cucumis sativus* L.) and the subsequent backcrossing with the second cucumber plant (*Cucumis sativus* L.). However, such conventional breeding methods are preferably assisted with molecular biology techniques to establish the maintenance of the present resistance genetic locus in the second cucumber plant (*Cucumis sativus* L.)

In a preferred embodiment, the second cucumber plant (*Cucumis sativus* L.) is a Cucumber Vein Yellowing Virus (CVYV) susceptible commercial variety. By transferring the present Cucumber Vein Yellowing Virus (CVYV) resistance genetic locus into this plant, while maintaining other commercially valuable high quality genotypic and phenotypic characteristics, a cucumber plant (*Cucumis sativus* L.) with increased economic value is provided.

In a most preferred embodiment, the present method provides a cucumber plant (*Cucumis sativus* L.) having the genotype of the second cucumber plant (*Cucumis sativus* L.) supplemented with a Cucumber Vein Yellowing Virus (CVYV) resistance genetic locus of the first cucumber plant (*Cucumis sativus* L.).

In a preferred embodiment of the present method, the present method comprises a step (c) comprising exposing said second cucumber plant (*Cucumis sativus* L.) to Cucumber Vein Yellowing Virus (CVYV) therby establishing resistance to the virus.

Considering the capacity of the primers comprising SEQ ID Nos. 1 and 2 to identify the present Cucumber Vein Yellowing Virus (CVYV) resistance genetic locus, an aspect of the present invention relates to the use of SEQ ID No: 1 and/or SEQ ID No: 2 for establishing the presence of a Cucumber Vein Yellowing Virus (CVYV) resistance conferring genetic element in a cucumber plant (*Cucumis sativus* L.)

The plants obtainable by the present method are resistant to Cucumber Vein Yellowing Virus (CVYV) and hence have economical advantages over Cucumber Vein Yellowing Virus (CVYV) susceptible plants such as providing increased yields.

Therefore, the present invention, according to another aspect, relates to Cucumber Vein Yellowing Virus (CVYV) resistant cucumber plants (*Cucumis sativus* L.) comprising a Cucumber Vein Yellowing Virus (CVYV) resistance conferring genetic element, wherein the presence of said Cucumber Vein Yellowing Virus (CVYV) resistance conferring genetic element in said cucumber plant (*Cucumis sativus* L.) is characterized by a nucleic acid amplification fragment of 245 to 247 base pairs, preferably 246 base pairs, using molecular amplified fragment length polymorphism (AFLP) primers SEQ ID No: 1 and SEQ ID No: 2 in a molecular amplified fragment length polymorphism (AFLP) assay using the genome of said cucumber plant (*Cucumis sativus* L.) as template for nucleic acid amplification.

In a preferred embodiment of this aspect of the present invention, the plants are cucumber plants (*Cucumis sativus* L.) of which the seeds are deposited at NCIBM under accession number NCIMB 41635.

According to a particularly preferred embodiment, the present invention relates to Cucumber Vein Yellowing Virus (CVYV) resistant cucumber plants (*Cucumis sativus* L.), wherein the plants are cucumber plants (*Cucumis sativus* L.) of which the seeds are deposited at NCIBM under accession number NCIMB 41635.

It should be understood that the present invention is not restricted to the plants as such but also relates to plants, plant parts, tissues, cells, and/or seeds derived from the present plants and the use thereof for providing Cucumber Vein Yellowing Virus (CVYV) resistance to other cucumber plants (*Cucumis sativus* L.).

According to a preferred aspect of the above use, besides providing or exhibiting Cucumber Vein Yellowing Virus (CVYV) resistance, the present plants, or plant or parts obtained or originating thereof, also provide Cucumber Green Mottle Mosaic virus (CGMMV) resistance, preferably Cucumber Green Mottle Mosaic virus (CGMMV) resistance and Cucumber Fruit Mottle Mosaic Virus (CFMMV) resistance.

EXAMPLES

Example 1

Cucumber Vein Yellowing Virus (CVYV) Resistance Conferring Genetic Element

Introduction

In this example, a Qualitative Trait Locus (QTL) genetically linked to a Cucumber Vein Yellowing Virus (CVYV) resistance conferring genetic element was identified in resistant cucumber plants (*Cucumis sativus* L.) by use of a Bulk QTL Analysis (BQA), performed by Keygene N.V., Wageningen, The Netherlands. A population for marker development for Cucumber Vein Yellowing Virus (CVYV) resistance was selected. A total of 96 AFLP primer combinations were screened on two pools containing individuals showing 'extreme phenotypes'. Subsequently, five candidate markers were verified on resistant and susceptible individuals.

Marker Identification and Verification

Leaf material of plants was obtained: a line 11366×OK561 population to provide the population to be tested, inbred lines of the donor parent line 11366 and the parental lines of the population. DNA was isolated and EcoRI/MseI templates were generated. A test fingerprint of the plants was generated using primer combination E14/M59.

BSA and Verification on Individuals

The BQA was performed by screening a total of 96 primer combinations on a pool containing ten 'extreme resistant' individuals and a pool containing ten 'extreme susceptible' individuals. This screening resulted in the identification of the following candidate markers:

E14/M58 F 169 P2; and

E22/M48 F 248/246 (bi allelic)

These markers were subsequently verified. Based on this verification the candidate markers identified proved to be linked to tobamovirus resistance.

Verification of Candidate Markers on the Population

After screening the 96 primer combinations and subsequent validation of the markers, one putative QTL could be identified. In order to determine whether the QTL identified is indeed a separate QTL a linkage analysis was executed.

Markers (E14/M58 F 169 P2 and the biallelic marker E22/M48 F 248/246) were screened on 46 additional individuals from the population.

A marker dataset was generated and merged with the marker dataset of the verification. Based upon this analysis, it could be concluded that the four markers are indeed linked to one QTL.

Marker Analysis Using WinQTLCartographer

In order to determine the correlation between the phenotype and genotype, the marker dataset was analyzed using the software package WinQTLCartographer. For Single Marker Analysis (SMA) a LOD value of 12 was calculated. For Interval Mapping (IM) the 95% reliable threshold was calculated by performing 1000 permutations on the phenotype data and was determined as LOD 0.9. The LOD value and percentage explained variances were calculated for this QTL (LOD: 9; Exp.Var.: 49.5).

Conclusion

In order to identify a QTL for Cucumber Vein Yellowing Virus (CVYV) resistance, a BQA was performed. A total of 96 primer combinations were screened on a bulk of ten 'extreme resistant' individuals and a bulk of ten 'extreme susceptible' individuals. Candidate markers, of which one was bi allelic, were verified on 'extreme resistant' and 'extreme susceptible' individuals and on other individuals of the population. A QTL region was identified by using a BQA approach. Based on the TestPC (~five markers) no heterogenity was identified in the 30 inbred lines of the resistant donor parent line 11366.

Example 2

Molecular Marker Assisted Identification of Cucumber Vein Yellowing Virus (CVYV) Resistance Resistant Cucumber Plants (*Cucumis sativus* L.)

Molecular Analysis

From both susceptible, i.e., showing one or more of the symptoms of a viral infection, and resistant individual cucumber plants (*Cucumis sativus* L.) genomic material was isolated using standard protocols.

Subsequently, this genomic material was digested using the appropriate restriction enzymes (EcoRI/MseI) and, after ligation of the adapters, subjected to AFLP nucleic acid amplification using primer pairs 5-GAC TGC GTA CCA ATT CGT-3' (SEQ: ID NO: 1) and 5'-GAT GAG TCC TGA GTA ACA C-3' (SEQ. ID NO: 2) or primer pair 5'-GAC TGC GTA CCA ATT CAT-3' (SEQ. ID NO: 3) and 5-GAT GAG TCC TGA GTA ACG T-3' (SEQ. ID NO: 4). The resulting amplification products were resolved by gel electrophoresis for size determination. The presence of AFLP markers in the genomes of the individual cucumber plants (*Cucumis sativus* L.) were detected as absent (−) or as present (+).

Specifically, when AFLP Marker E14/M58-F-169 (not encompassed by the present invention, primer pair 5'-GAC TGC GTA CCA ATT CAT-3' and 5-GAT GAG TCC TGA GTA ACG T-3') was present, a band of approximately 169 by was observed; when AFLP Marker E22/M48-F-248 (not encompassed by the present invention, primers 5-GAC TGC GTA CCA ATT CGT-3' and 5'-GAT GAG TCC TGA GTA ACA C-3') was present, a band of approximately 248 by was observed. AFLP marker E14/M48-F-246 (encompassed by the present invention, primers 5-GAC TGC GTA CCA ATT CGT-3' and 5'-GAT GAG TCC TGA GTA ACA C-3') with an estimated size of approximately 246 by genetically correlated with the resistant phenotype The results are summarized in Table 1 below.

TABLE 1

Correlation between AFLP markers E14/M58 F 169; E22/M48 F 246; and E22/M48 F 248 and a Cucumber Vein Yellowing Virus (CVYV) resistance phenotype

| Individual cucumber plants (*Cucumis sativus* L.) | Phenotype | E14/M58-F-169 | E22/M48-F-246 | E22/M48-F-248 |
|---|---|---|---|---|
| TLCG04_4816_10 | susceptible | + | − | + |
| TLCG04_4816_18 | susceptible | + | − | + |
| TLCG04_4816_13 | susceptible | + | − | + |
| TLCG04_4816_23 | susceptible | + | − | + |
| TLCG04_4816_24 | susceptible | + | − | + |
| TLCG04_4816_31 | susceptible | + | − | + |
| TLCG04_4816_43 | susceptible | + | − | + |
| TLCG04_4816_56 | susceptible | + | − | + |
| TLCG04_4816_57 | susceptible | + | − | + |
| TLCG04_4816_61 | susceptible | + | − | + |
| TLCG04_4816_64 | susceptible | + | − | + |
| TLCG04_4816_66 | susceptible | + | − | + |
| T33168_4 | resistant | − | + | − |
| T33168_5 | resistant | − | + | − |
| T33169_9 | resistant | − | + | − |
| T33168_2 | resistant | − | + | − |
| T33168_6 | resistant | − | + | − |
| T33168_7 | resistant | − | + | − |
| T33168_8 | Resistant | − | + | − |
| T33168_9 | resistant | − | + | − |
| T33169_2 | resistant | − | + | − |
| T33169_3 | resistant | − | + | − |
| T33169_5 | resistant | − | + | − |
| T33169_6 | resistant | − | + | − |
| NCIMB 41635 | resistant | − | + | − |

Table 1 clearly shows that a Cucumber Vein Yellowing Virus (CVYV) resistance phenotype in all cucumber plants (*Cucumis sativus* L.) tested is genetically linked with the presence of molecular AFLP marker E22/M48-F-246. Thus, the detecting this marker indicates the presence of a Cucumber Vein Yellowing Virus (CVYV) resistance conferring genetic element or QTL.

Example 3

Marker E22/M48-F-246, Indicating the Presence of a Cucumber Vein Yellowing Virus (CVYV) Resistance Conferring Genetic Element Additionally Indicates the Presence of a Cucumber Green Mottle Mosaic Virus (CGMMV) Resistance Resistance Conferring Genetic Element and/or a Cucumber Fruit Mottle Mosaic Virus (CFMMV) Resistance Conferring Genetic Element Cucumber Vein Yellowing Virus (CVYV) resistance plants were also tested for Cucumber Green Mottle Mosaic virus (CGMMV) resistance and Cucumber Fruit Mottle Mosaic Virus (CFMMV) resistance. Surprisingly, all CVYV resistant plants tested, also showed an absolute pleiotropic resistance to Cucumber Vein Yellowing Virus (CVYV), Cucumber Green Mottle Mosaic virus (CGMMV) and Cucumber Fruit Mottle Mosaic Virus (CFMMV) as shown in the below presented Table 2 of a OK561×line 11366 segregating DH population. All resistant (indicated as R) plants shown were positive for marker E22/M48-F-246 and negative for markers E14/M58-F-169 and E22/M48-F-248. Vice versa, All susceptible (indicated as S) plants shown were negative for marker E22/M48-F-246 and positive for markers E14/M58-F-169 and E22/M48-F-248.

TABLE 2

OK561 × line 11366 segregating DH population

| #DH | CVYV | CGMMV | CFMMV |
|---|---|---|---|
| 36 | R | R | R |
| 0 | R | S | S |
| 0 | S | R | R |
| 54 | S | S | S |
| Total 90 | | | |

The scores in the table indicate that the linkage between CGMMV, CFMMV and CVYV resistance is absolute thus a pleiotropic effect

TABLE 3 line panel

| CVYV | CGMMV | #lines |
|---|---|---|
| R | R | 52 |
| R | R | 0 |
| R | S | 7 |
| R | S | 1 |
| S | S | 10 |
| S | S | 35 |
| S | R | 0 |
| S | R | 0 |

Table 3 clearly shows that CGMMV resistant lines are always CVYV resistant because no recombinants could be found but CVYV lines are not always CGMMV resistant. Hence, marker E22/M48-F-246 is indicative for both CVYV and CGMMV resistance, however other CVYV resistances not linked to CGMMV resistance and marker E22/M48-F-246 exist.

The invention claimed is:

1. A method of making a Cucumber Vein Yellowing Virus (CVYV) and Cucumber Green Mottle Mosaic Virus (CGMMV) resistant cucumber plant (*Cucumis sativus* L.) comprising:
   a) providing a first cucumber plant (*Cucumis sativus* L.), wherein said first cucumber plant is a cucumber plant (*Cucumis sativus* L.) deposited at NCIBM under accession number 41635, said first cucumber plant comprising a Cucumber Vein Yellowing Virus (CVYV) and Cucumber Green Mottle Mosaic Virus (CGMMV) resistance conferring genetic element;
   b) transferring the identified Cucumber Vein Yellowing Virus (CVYV) and Cucumber Green Mottle Mosaic Virus (CGMMV) resistance conferring genetic element into a second cucumber plant (*Cucumis sativus* L.) thereby conferring Cucumber Vein Yellowing Virus (CVYV) and Cucumber Green Mottle Mosaic Virus (CGMMV) resistance to said second cucumber plant (*Cucumis sativus* L.), wherein said transferring comprises detecting a nucleic acid amplification fragment of 245 to 247 base pairs using molecular amplified fragment length polymorphism (AFLP) primers SEQ ID NO: 3 and SEQ ID NO: 4 in a molecular amplified fragment length polymorphism (AFLP) assay using the genome of said second cucumber plant (*Cucumis sativus* L.) as template.

2. The method according to claim 1, wherein said method further comprises a step (c) comprising exposing said second cucumber plant (*Cucumis sativus* L.) to Cucumber Vein Yellowing Virus (CVYV) and Cucumber Green Mottle Mosaic Virus (CGMMV).

3. The method according to claim 1, wherein said nucleic acid amplification fragment is 246 bp.

* * * * *

UNITED STATES PATENT AND TRADEMARK OFFICE
CERTIFICATE OF CORRECTION

PATENT NO. : 8,779,241 B2
APPLICATION NO. : 13/382770
DATED : July 15, 2014
INVENTOR(S) : Mazereeuw et al.

It is certified that error appears in the above-identified patent and that said Letters Patent is hereby corrected as shown below:

In the Claims

Column 9, Line 55, Claim 1, delete "NCIBM" and insert -- NCIMB --

Signed and Sealed this
Fourth Day of November, 2014

Michelle K. Lee
*Deputy Director of the United States Patent and Trademark Office*

SEQUENCE LISTING

<160> NUMBER OF SEQ ID NOS: 4

<210> SEQ ID NO 1
<211> LENGTH: 18
<212> TYPE: DNA
<213> ORGANISM: Artificial
<220> FEATURE:
<223> OTHER INFORMATION: molecular amplified fragment length
      polymorphism (AFLP) primer 1

<400> SEQUENCE: 1
gactgcgtac caattcgt                                                 18

<210> SEQ ID NO 2
<211> LENGTH: 19
<212> TYPE: DNA
<213> ORGANISM: Artificial
<220> FEATURE:
<223> OTHER INFORMATION: molecular amplified fragment length
      polymorphism (AFLP) primer 2

<400> SEQUENCE: 2
gatgagtcct gagtaacac                                                19

<210> SEQ ID NO 3
<211> LENGTH: 18
<212> TYPE: DNA
<213> ORGANISM: Artificial
<220> FEATURE:
<223> OTHER INFORMATION: molecular amplified fragment length
      polymorphism (AFLP) primer 3

<400> SEQUENCE: 3
gactgcgtac caattcat                                                 18

<210> SEQ ID NO 4
<211> LENGTH: 19
<212> TYPE: DNA
<213> ORGANISM: Artificial
<220> FEATURE:
<223> OTHER INFORMATION: molecular amplified fragment length
      polymorphism (AFLP) primer 4

<400> SEQUENCE: 4
gatgagtcct gagtaacgt                                                19